United States Patent [19]
Bohnenpoll geb. Hinners

[11] Patent Number: 4,751,088
[45] Date of Patent: Jun. 14, 1988

[54] PROCEDURE FOR REDUCING AN ACID SURPLUS IN THE FERMENTATION OF ALCOHOL

[75] Inventor: Auguste Bohnenpoll geb. Hinners, Hoheging, Fed. Rep. of Germany

[73] Assignee: Georg Westphal Ing. KG., Offenbach, Fed. Rep. of Germany

[21] Appl. No.: 890,640

[22] Filed: Jul. 25, 1986

[30] Foreign Application Priority Data

Oct. 2, 1985 [DE] Fed. Rep. of Germany ....... 3535150

[51] Int. Cl.$^4$ .................... C12C 11/00; C12H 1/00
[52] U.S. Cl. .................. 426/11; 426/330.4; 426/592
[58] Field of Search ............. 426/11, 14, 15, 16, 426/29, 592, 600, 321, 330.4, 269

[56] References Cited

U.S. PATENT DOCUMENTS 2,206,066 7/1940 Wallerstein ............... 426/330.4
2,658,829 11/1953 MacDonough ............ 426/330.4

Primary Examiner—Raymond N. Jones
Assistant Examiner—Marianne M. Cintins
Attorney, Agent, or Firm—Klein and Vibber

[57] ABSTRACT

A process is described by which the addition of sodium sulfite reduces acid surplus during alcohol fermentation, for the purpose preventing a detrimental reduction to pH value and maintaining the pH at a generally constant level.

2 Claims, No Drawings

PROCEDURE FOR REDUCING AN ACID SURPLUS IN THE FERMENTATION OF ALCOHOL

This invention concerns the reduction of an acid surplus in the fermentation of alcohol, particularly in mash, in which dealcoholized, decanted mash is used as processing water, for the purpose of preventing a decrease in the pH value and holding said value generally constant.

BACKGROUND OF THE INVENTION

Currently, decanted, dealcoholized mash is frequently used as processing water (in a recycling process) in order to minimize waste water and its disposal. However, dealcoholized mash, also called slop or distiller's wash, contributes acid to the process and causes an increase in the pH. As a rule, the acid is neutralized with a leaching solution, such as brine or lime. A disadvantage of this process is that neutralization produces detrimental salts, i.e. they inhibit the fermentation process.

A consistently stable pH value is an essential factor in alcoholic fermentation. The most favorable value for the main saccharification of sweet mash in steam mashing lies generally in the range 5.3 to 5.7. As a result of the formation of natural acid due to yeast and, at times, due to "false" acid resulting from infection organisms, the pH value decreases during the process of fermentation; normally most pronounced during the fermentation as a result of the yeast growth. The lowest limits of the pH value required for the individual mash types (4.2 to 4.3 or 4.5 to 4.6) can generally be securely maintained during uninterrupted operation. However, should any form of infection occur, primarily due to bacteria introduced from the environment, as is especially possible during recycling, then the acid content, under certain circumstances, will increase dramatically, whereby the pH value will fall below the required level.

An acid increase that is too high also jeopardizes the post saccharification process and thereby the post fermentation products; and also is a disadvantage because sugar or accohol is consumed to form the acid. An execcsivly strong or rapid acid buildup, therefore, has both a direct and an indirect detrimental effect on the yield. An infection, especially by way of certain lactic or butyric acid bacteria, is damaging for the yeast or can even be a strong yeast poison.

In the past it has been recommended to maintain a high pH value in alcohol fermentation with sulfuric or hydrochloric acid, and a low pH value with calcium hydroxide. However, such regulation, by way of acid or base additives, requires a relatively exact dose in order to avoid the respective opposite result. Furthermore, care must be taken with regard to the formation of salts during the continuous exchange from neutralization to acidification.

SUMMARY OF THE INVENTION

It is the object of the present invention to create a process for the reduction of surplus acid during alcohol fermentation that allows for a secure and simple regulation of the pH value during fermentation.

This object is achieved by way of a recycling process in which dealcoholized, decanted mash is used as processing water, as described above, wherein sodium sulfite is added to the fermenting mass, preferably during the beginning of fermentation.

It has been discovered that by adding sodium sulfite under conditions of gas formation, whereby $SO_2$ escapes with $CO_2$, an acid surplus is effectively reduced and the formation of surplus acid in inhibited. In principle the process behaves as follows:

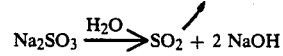

Acetic acid, lactic acid and butyric acid are often present in the fermenting mass, and enter the mass by way of infection. The following reactions result from the addition of sodium sulfite according to the invention:

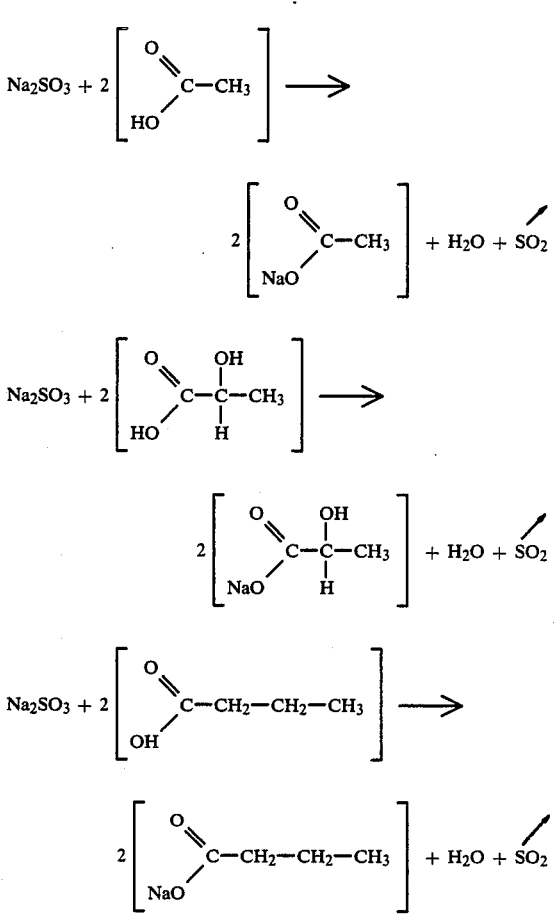

Caustic soda solution (soda lye) results from the decomposition of sodium sulfite and reacts with the acids to form the corresponding salts, water and $SO_2$ which escapes as gas. By this means a corresponding amount of acid is neutralized and the pH value is maintained at a desirable level. The pH value of the slop (distiller's wash) can be easily regulated by way of this simple measure, without fear of any detrimental effects.

For practical purposes the sodium sulfite should be added during the beginning of fermentation and adjusted during the fermentation process when an increase in acidity or a corresponding decrease in pH is observed.

The sodium sulfite dosage can be determined manually or by automation, by means of pH measurement, signal utilization, and a dosing apparatus. Facilities of this type are available from the present state of the art. The costs involved for such implementation compare favorably to other methods of slop removal.

We claim:

1. A process for the neutralization of acidity during alcohol fermentation of a fermenting mass, in which a dealcoholized, decanted mash is used as processing water, comprising the step of adding sodium sulfite to the fermenting mass in an amount sufficient to keep the pH-value in the range of 5.3 to 5.7.

2. A process for the neutralization of acidity during alcohol fermentation of a fermenting mass, in which a dealcoholized, decanted mash is used as processing water, comprising the step of adding sodium sulfite to the fermenting mass at the beginning of fermentation, of said mass, in an amount sufficient to keep the pH-value in the range of 5.3 to 5.7

* * * * *